United States Patent [19]
Koci

[11] Patent Number: 4,731,070
[45] Date of Patent: Mar. 15, 1988

[54] ADULT INCONTINENT ABSORBENT ARTICLE

[75] Inventor: Shirley A. Koci, Monmouth Junction, N.J.

[73] Assignee: Personal Products Company, Milltown, N.J.

[21] Appl. No.: 883,204

[22] Filed: Jul. 8, 1986

Related U.S. Application Data

[63] Continuation of Ser. No. 601,830, Apr. 19, 1984, abandoned.

[51] Int. Cl.$^4$ ............................................. A61F 13/16
[52] U.S. Cl. ............................................. 604/385 R
[58] Field of Search ............... 604/385.1, 389, 390, 604/391, 386, 387

[56] References Cited

U.S. PATENT DOCUMENTS

| | | | |
|---|---|---|---|
| 3,731,688 | 5/1973 | Litt et al. | 604/385.1 |
| 3,874,385 | 4/1975 | Gellert | 604/385.1 |
| 3,929,134 | 12/1975 | Karami | 604/385.1 |
| 3,938,523 | 2/1976 | Gilliland | 604/385.1 |
| 3,939,837 | 2/1976 | Taylor | 604/385.1 |
| 3,968,799 | 7/1976 | Schrading | 604/385.1 |
| 4,108,179 | 8/1978 | Schaar | 604/385.1 |
| 4,230,113 | 10/1980 | Mehta | 604/385.1 |

Primary Examiner—John D. Yasko
Attorney, Agent, or Firm—Martha A. Michaels; Lawrence D. Schuler

[57] ABSTRACT

An absorbent article particularly suitable for use by male and female adult incontinents. The absorbent article includes a urine receptacle pocket offset to one end of the product and formed by folding the product and adhering together portions of a moisture impervious sheet that are folded over side marginal edges of an absorbent batt.

10 Claims, 5 Drawing Figures

ADULT INCONTINENT ABSORBENT ARTICLE

This is a continuation, of application Ser. No. 601,830, filed Apr. 19, 1984, now abandoned.

TECHNICAL FIELD OF THE INVENTION

This invention relates to absorbent articles suitable for use as an adult incontinent garment, and more particularly to a disposable undergarment that will accommodate both male and female incontinents.

BACKGROUND OF THE INVENTION

Disposable diapers have been in widespread use for many years. Typical generally rectangularly shaped prior art disposable diaper constructions are shown in Duncan et al U.S. Pat. No. Re. 26,151 and Mesek et al U.S. Pat. No. 3,612,055. It has also been known to provide shaped or contoured disposable diapers, such as an hourglass shape or a T-shape, and Buell U.S. Pat. No. 3,860,003 and Widland U.S. Pat. No. 3,768,479 are typical of such constructions.

In the more recent past, it has been proposed to provide disposable absorbent articles for incontinent adults. Not surprisingly, designers of disposable incontinent adult products have looked and generally followed the teachings of the disposable diaper art. For example, a typical prior art disposable adult incontinent product is shown in Strickland et al U.S. Pat. No. 4,253,461. Because of the anatomical differences between adults and infants, one cannot simply increase the dimensions of a baby diaper and expect the resulting product to function satisfactorily as an incontinent adult product.

While comfortable and inconspicuous fit and moisture containment are desirable in baby diapers, they are absolutely essential for a successful adult incontinent product. Unfortunately, adult incontinent products that are presently available are bulky, uncomfortable, noisy and provide inadequate protection against moisture leakage. As a result, there remains a need for an improved disposable product suitable for use by the large number of adults that have incontinence problems.

SUMMARY OF THE INVENTION

According to the present invention, a narrow, contoured absorbent article is provided with an essentially moisture impervious urine receptacle pocket at one end thereof. The absorbent article of the present invention not only provides improved moisture containment, but it also can be comfortably fitted about an adult torso so as to be inconspicuous when worn under other garments. While the structure of the present invention has particular use in an incontinent adult product, it also has utility in baby diapers, and the term "absorbent article" as used herein and in the appended claims is intended to encompass and include diapers, incontinent pads and other similar products.

In accordance with one aspect of the present invention, the absorbent article is provided with a moisture impervious sheet on one side or surface of an absorbent batt, with side flap portions of the moisture impervious sheet being folded over the opposite body facing side or surface of the absorbent batt. A moisture pervious facing liner is provided at least at the body facing side of the absorbent article, and preferably the liner completely encases the absorbent batt and the moisture impervious sheet to give the product a cloth-like feel.

The absorbent article of the present invention is folded, at least in the crotch portion, inwardly about spaced, parallel first fold lines and outwardly about spaced, parallel second fold lines. The inwardly extending portions of the moisture impervious sheet extend inwardly past the second fold lines, so as to dispose inner edge sections of the inwardly extending portions in facing relationship with respect to one another. The facing inwardly extending portions are secured to one another to provide a narrowed crotch region. The folded over and inwardly extending moisture impervious sheet portions prevent absorbed liquid from leaking at the sides of the product, and form a urine receptacle pocket. The inwardly extending portions are secured together at a location offset toward the rear of the product, so that the urine receptacle pocket is located toward the front of the product making it suitable for use by both male and female incontinent adults.

DESCRIPTION OF THE PREFERRED EMBODIMENT

Figure 1:
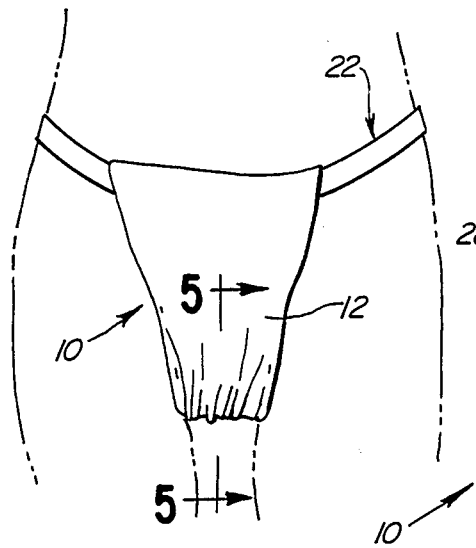
FIG. 1 is a front view of the absorbent product of the present invention applied to the torso of an adult.

While this invention is susceptibel of embodiment in many different forms, there is shown in the drawing and will herein be described in detail a preferred embodiment, with the understanding that the present disclosure is to be considered as an exemplification of the principles of the invention and is not intended to limit the invention to the embodiment illustrated. The scope of the invention will be pointed out in the appended claims.

Figure 2:
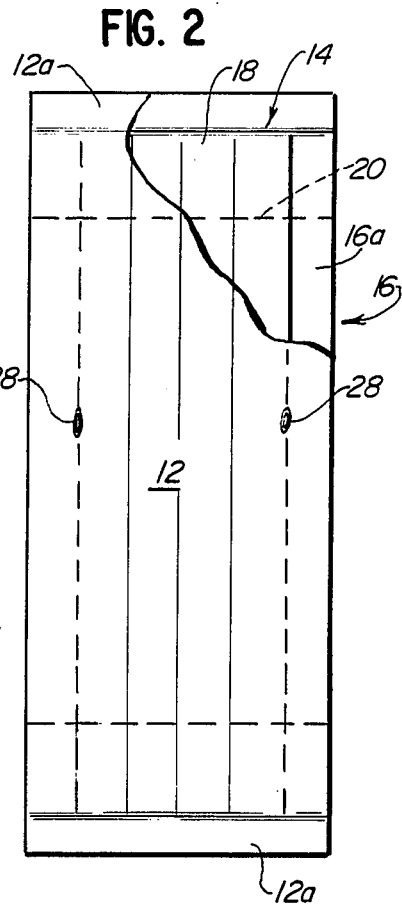
FIG. 2 is a plan view of the product of the present invention prior to folding, with a portion broken for clarity of internal detail.

Referring now to the drawing, the absorbent article 10 of the present invention includes a moisture pervious liner 12, an absorbent batt 14, and a moisture impervious sheet 16. In the illustrated embodiment, absorbent batt 14 includes a first batt layer 18 and a second batt layer 20. Both batt layers are generally rectangular in shape and equal in width dimension. Batt layer 18 is larger than batt layer 20, and extends outwardly from each end of batt layer 20 by a substantially equal amount, as can be best seen in FIG. 2.

Moisture impervious sheet 16 is also generally rectangular in shape and coterminous in the length dimension with batt layer 18. Sheet 16 is wider than batt layers 18 and 20, which are centered on sheet 16, to define generally rectangularly shaped moisture impervious side flaps 16a that are folded over the side marginal edges of both batt layers. The flap portions provide a moisture containment barrier along the entire length of both side marginal edges of the batt, and provide inwardly extending moisture impervious portions on batt layer 18.

Moisture pervious liner 12 is also generally rectangularly shaped in the illustrated embodiment and is longer than batt layer 18 and moisture impervious layer 16 to define liner end portions 12a that extend outwardly a substantially equal amount at each end of the absorbent product. Liner 12 has a width dimension greater than twice that of batt layers 18 and 20, so that when liner 12 is folded to completely envelop batt 14 and moisture impervious sheet 16, a longitudinally extending lap joing 12b is created. While it is preferred that the liner be present at both sides of the absorbent product of the present invention to give the product a cloth-like feel, the liner may be present only on the body facing side of the product. When an overall liner is used, as shown, it is preferred to locate the lap seam 12b on the outer side of the absorbent article.

Liner 12 is secured to itself in end portions 12a and lap seam 12b by lines of adhesive, or by heat sealing, if the liner is formed of a thermoplastic material. Liner 12 and moisture impervious sheet 16 may also be secured to batt layer 20 by spaced lines of adhesive, or by other suitable means, if desired. The absorbent product 10 is secured about the torso of the wearer by any suitable securement means 22, such as that shown in Bolick U.S. Pat. No. 4,315,508.

Several different types of liner materials may be used. For example, the liner may be a non-woven web made of a mixture of fibers consisting predominantly of inexpensive, short, cellulosic fibers such as short wood pulp fibers or cotton liners in amounts of 75 percent to 98 percent, the balance being textile length fibers such as rayon as described in U.S. Pat. No. 3,668,348 to Liloia, et al.

Non-woven liner materials suitable for use in absorbent articles of this invention can have weights in the range of from about 0.5 to 5 ounces per square yard and densities of less than 0.15 g/cc., generally in the range of 0.05 to about 0.1 g/cc. The dry strength of the liner for a fabric having a weight of about 1.5 ounces per square yard is at least 0.15 lbs. per inch of width in the machine direction and at least 0.1 lb. per inch of width in the cross direction. Such fabrics have good elongation, loft, softness, and drape characteristics. Liners may also be made of an apertured non-woven fabric which is formed, for example, in accordance with the teachings of commonly assigned U.S. Pat. Nos. 2,862,251; 3,081,514; and 3,081,515. Furthermore, liners may also be made from other types of fabric such as those disclosed and described in U.S. Pat. No. 3,485,706 to Evans. Such liners can be made of naturally occurring fibers, synthetic fibers or blends thereof. Typical liners made of polyester type fibers may have a weight of about 0.75 ounces per square yard.

In addition, liners may be made from non-apertured materials such as non-woven isotropic webs or apertured polyolefin or polyester films having the desired permeability. In all of the aforementioned liners, the materials should be relatively hydrophobic so as to retard wicking within the lining.

A suitable backing material for the absorbent articles embodying the present invention can be an opaque polyolefin; for example, polyethylene about 0.001 inch thick. Another suitable material for this purpose is polyethylene terephthalate having a thickness of about 0.005 inch.

The absorbent batt layers preferably are formed of loosely compacted short cellulose fibers, such as wood pulp fibers, or cotton liners, or mixtures thereof, which primarily are held together by interfiber bonds requiring little or no added adhesive, as is known in the art. Briefly these batts are a low bulk density coherent web of loosely compacted cellulose fibers, preferably comminuted wood pulp fibers, in the form of so-called "fluff".

The term "short fibers" as used herein, refers to fibers less than about ¼ inch in length, in contrast to "long fibers" or "textile length fibers" which are longer than about ¼ inch in length, and generally are between ½ and 3 inches in length.

Preferably the absorbend batt layer 20 includes a paper-like, densified compacted cellulosic fibrous layer of relatively high wettability and relatively high fluid retentivity integral with the batt on the side thereof in contact with the backing sheet 16. The paper-like densified layer is formed by slight moistening of one surface of the batt followed by the application of pressure thereto. This densified skin portion provides a wickability gradient to draw urine from the more loosely compacted cellulosic fibrous layers into the densified layer. The densified layer portion is described in more detail in Burgeni U.S. Pat. No. 3,017,304.

The composite density of the absorbent batt should be above about 0.07 gm/cc. and preferably between about 0.10 and 0.15 gm/cc. The foregoing density values are applicable to the absorbent product produced. In storage and handling, the loft or thickness of the batt is increased to some extent, resulting in lower densities.

The densified layer preferably includes regions of increased thickness dimension for adding strength to the batt layer 20 and providing a further wicking mechanism. Such regions may be formed in accordance with the teachings of Repke U.S. Pat. No. 3,938,522.

Alternatively, the wicking layer may be provided by a wicking member separate from the batt layer 20, such as a wet strength tissue wicking layer. With such an arrangement, superabsorbent materials may be secured to, or loosely distributed on, the side of the tissue layer in contact with batt layer 20. Suitable superabsorbent materials are disclosed, for example, in U.S. Pat. No. 4,327,728 and 4,333,463.

Figure 4:
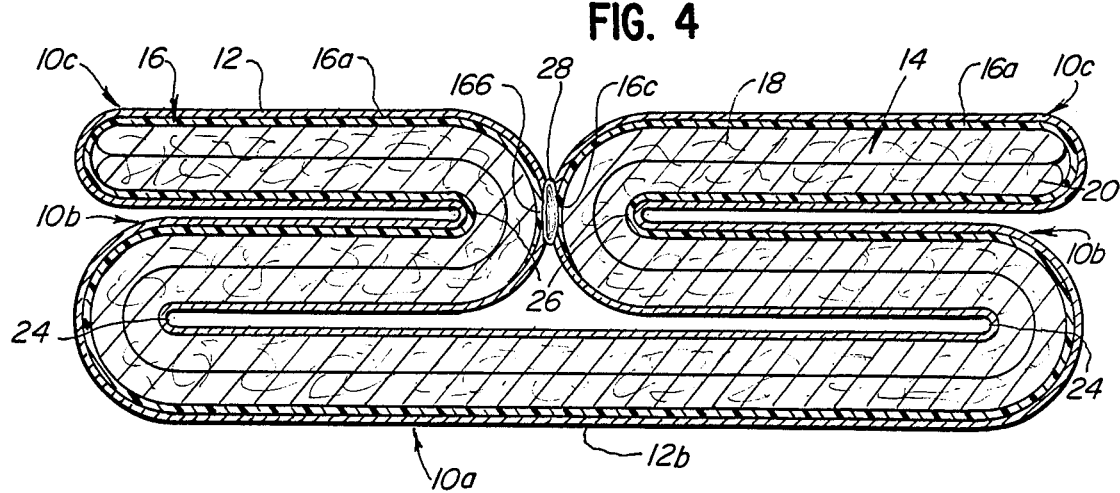
FIG. 4 is an enlarged cross-sectional view taken generally along line 4—4 of FIG. 3.

In accordance with an important aspect of the present invention, the absorbent article 10 is folded, preferably from end to end, into the configuration of FIG. 4. More specifically, intermediate portions 10b, approximately one-sixth the overall width of the absorbent article, are folded inwardly about spaced, parallel first fold lines 24 into overlying relationship with central portion 10a, approximately one-third the overall width of the absorbent article. Outer portions 10c, approximately one-sixth the overall width of the absorbent article, are then folded outwardly about spaced, parallel second fold lines 26 into overlying relationship with intermediate portions 10b.

Figure 3:
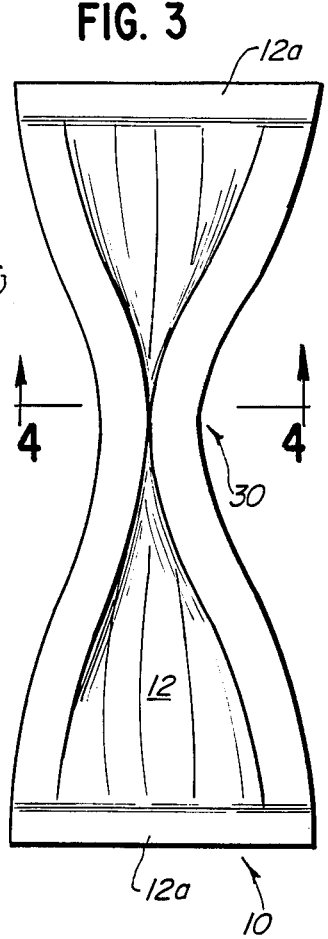
FIG. 3 is a plan view similar to FIG. 2, but showing the article of the present invention just prior to being put on by the wearer.
Figure 5:
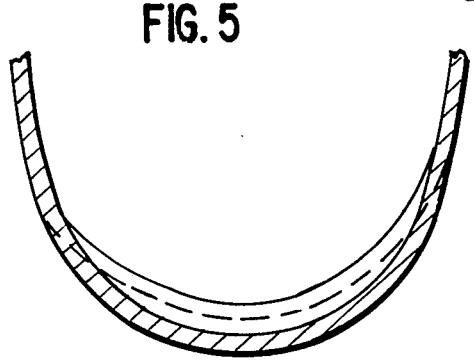
FIG. 5 is a cross-sectional view taken generally along line 5—5 of FIG. 1.

Side flap portions 16a of the moisture impervious sheet extend inwardly beyond the second fold lines 26, so that when the absorbent article is folded as described above, innermost sections 16c of the moisture impervious sheet are disposed in facing relationship with one another. Sections 16c are secured together, as by a bead or globule of adhesive 28, which penetrates through the liner 12 and securely bonds sheet sections 16c together. Securement means 28 need not have any substantially longitudinal extent, but must be sufficiently secure to retain the crotch portion 30 of the absorbent article in a reduced width configuration, as can be best seen in FIG. 3.

In a specific example of the present invention, batt layer 18 has a width dimention of 8 inches and a length dimension of 19 inches. Liner 12 has a length dimension of 22 inches, and liner end portions 12a are each 1½ inches. Sheet portions 16a extend inwardly 1½ inches from each side marginal edge of the batt, a distance slightly greater than the 1⅜ inch that the second fold lines are spaced inwardly of the side marginal edges of the absorbent product. Glue tack 28 is offset longitudinally from the center toward the rear of the absorbent article, by about 2½ inches to create the urine receptacle pocket at the front of the absorbent article. For absorbent articles of the same overall dimensions, i.e., 8 inches ×22 inches, it is contemplated that the securement means 28 may be offset from the longitudinal center line toward the rear of the absorbent article in the range of from about 2 inches to about 4 inches and yet provide the desired urine receptacle pocket that will accommodate both male and female adult incontinents.

The resulting structure provides not only improved liquid containment, but also improved fit and comfort. The scope of the invention is pointed out in the appended claims.

What is claimed is:

1. An absorbent article comprising: an absorbent batt having opposite major faces; a moisture impervious sheet covering one major face of said batt, said moisture impervious sheet being wider than said batt and including flap portions folded over opposite side marginal edges of said batt and providing inwardly extending, spaced, moisture impervious sheet portions disposed against the other major face of said absorbent batt; a moisture pervious liner covering the other major face of said absorbent batt and at least the inwardly extending portions of said moisture impervious sheet; said absorbent article being folded so as to dispose inner edge sections of said inwardly extending moisture impervious sheet portions in facing relationship with respect to one another; said inner edge sections of said inwardly extending moisture impervious sheet portions being covered by overlying portions of said moisture pervious liner, and means acting through said overlying portions of said moisture pervious liner for securing said inner edge sections of said inwardly extending moisture impervious sheet portions to one another, said securing means being offset toward one end of said absorbent article to thereby define a urine receptable pocket at the opposite end of said absorbent article.

2. An absorbent article as set forth in claim 1 in which said batt and said moisture impervious sheet are rectangularly shaped, and wherein said batt is disposed centrally with respect to said moisture impervious sheet, whereby the inwardly extending portions of said moisture impervious sheet are rectangularly shaped and equal in size.

3. An absorbent article as set forth in claim 2 wherein the length dimensions of said moisture impervious sheet and said batt are the same.

4. An absorbent article as set forth in claim 3 in which at least the crotch portion of said absorbent article is folded inwardly about spaced, parallel first fold lines and outwardly about spaced, parallel second fold lines inwardly of said first fold lines; and wherein said inwardly extending portions of said moisture impervious sheet extend inwardly of said second fold lines.

5. An absorbent article as set forth in claim 4 wherein said securing means is provided by a bead of adhesive.

6. An absorbent article as set forth in claim 5 in which said moisture pervious liner is longer than said moisture impervious sheet to define end portions of said liner outwardly of the ends of said moisture impervious sheet.

7. An absorbent article as set forth in claim 6 in which said moisture pervious liner is more than twice the width of said batt, and wherein said liner is wrapped around said batt to define an overlapping seam extending longitudinally of said absorbent article.

8. An absorbent article as set forth in claim 7 wherein said overlapping seam is provided in the side of said article opposite from said inwardly extending moisture impervious sheet portions.

9. An absorbent article comprising: an absorbent batt having opposite major faces; a moisture impervious sheet covering one major face of said batt, said moisture impervious sheet being wider than said batt and including flap portions folded over opposite side marginal edges of said batt and providing inwardly extending, spaced, moisture impervious sheet portions disposed against the other major face of said absorbent batt; a moisture pervious liner covering the other major face of said absorbent batt and at least the inwardly extending portions of said moisture impervious sheet; at least the crotch portion of said absorbent article being folded inwardly about spaced, parallel first fold lines and outwardly about spaced, parallel second fold lines inwardly of said first fold lines, said inwardly extending portions of said moisture impervious sheet extending inwardly of said second fold lines so as to dispose inner edge sections of said inwardly extending moisture impervious sheet portions in facing relationship with respect to one another; said inner edge sections of said inwardly extending moisture impervious sheet portions being covered by overlying portions of said moisture pervious liner, and means acting through said overlying portions of said moisture pervious liner for securing said inner edge sections of said inwardly extending moisture impervious sheet portions to one another, said securing means being offset toward one end of said absorbent article to thereby define a urine receptable pocket at the opposite end of said absorbent article.

10. An absorbent article as set forth in claim 9 wherein said moisture pervious liner completely envelops said absorbent batt and said moisture impervious sheet.

* * * * *